United States Patent
Orsak (10) Patent No.: US 6,793,655 B2
(45) Date of Patent: Sep. 21, 2004

(54) EXTERNAL FIXATOR FOR DISTAL RADIUS FRACTURES

(75) Inventor: James E. Orsak, Huntersville, NC (US)

(73) Assignee: Smith & Nephew, Inc., Memphis, TN (US)

(*) Notice: Subject to any disclaimer, the term of this patent is extended or adjusted under 35 U.S.C. 154(b) by 126 days.

(21) Appl. No.: 10/293,962

(22) Filed: Nov. 13, 2002

(65) Prior Publication Data

US 2003/0109879 A1 Jun. 12, 2003

Related U.S. Application Data

(63) Continuation of application No. 09/530,760, filed as application No. PCT/US97/20258 on Nov. 4, 1997, now Pat. No. 6,491,694, which is a continuation-in-part of application No. 08/349,323, filed on Dec. 5, 1994, now Pat. No. 5,683,389.

(51) Int. Cl.[7] .............................................. A61B 17/56
(52) U.S. Cl. ........................................................ 606/57
(58) Field of Search ............................. 606/53, 54, 55, 606/59, 57, 105

(56) References Cited

U.S. PATENT DOCUMENTS

| 554,284 A | 2/1896 | Lorang |
| 575,631 A | 1/1897 | Brooks |
| 1,271,792 A | 7/1918 | Standish |
| 1,563,242 A | 11/1925 | Tweit |
| 2,250,417 A | 7/1941 | Ettinger |
| 2,251,209 A | 7/1941 | Stader |

(List continued on next page.)

FOREIGN PATENT DOCUMENTS

| CH | 02 709/94-3 | 9/1994 |
| DE | 375 151 | 5/1923 |
| DE | 1 935 977 | 2/1971 |
| DE | 1 603 999 | 5/1971 |
| DE | 38 05 178 A1 | 8/1989 |
| DE | 38 23 746 A1 | 1/1990 |
| DE | 91 03 480.9 | 6/1991 |
| DE | 295 12 917 U1 | 11/1995 |
| EP | 0 524 441 A1 | 6/1992 |
| EP | 0 700 664 A1 | 3/1996 |
| FR | 2 665 353 A | 2/1992 |
| NO | 25934 | 6/1915 |
| SU | 167008 | 11/1965 |
| SU | 1491-492 A1 | 8/1986 |
| SU | 1572590 A1 | 6/1990 |
| WO | WO 88/01152 | 2/1988 |
| WO | WO 94/18898 | 9/1994 |
| WO | WO 99/22661 | 5/1999 |

OTHER PUBLICATIONS

Agee, "External Fixation: Technical Advances Based Upon Multiplanar Ligamentotaxis," *Orthopedic Clinics of North America*, 24(2) (Apr. 1993).
Hoffmann II External Fixation System, 3 pages (Oct. 15, 2001) http://www.osteonics.com/howmedica/products/frames/prod2p.10.htm.
Search Report for European patent EP 92 11 0526.
Smith & Nephew Brochure entitled "Only from Smith & Nephew The Original Ilizarov System," six pages (01/99).

*Primary Examiner*—Eduardo C. Robert
(74) *Attorney, Agent, or Firm*—Kilpatrick Stockton LLP (57) ABSTRACT

An external fixator for fixating fractures provides an elongated support rod that includes proximal and distal rod sections. Fixation pins are provided for engaging the patient's bone tissue on opposite sides of a fracture. Clamps are rotatably supported upon the proximal rod section and distal rod section, each of the clamps being movable in rotational fashion both with respect to the rod and with respect to the pins. At least one of the clamps has articulating portions that rotate and angulate relative to one another so that total adjustment is provided between the rod and the pins. The articulating portion can be rigidified using one set fitting or set screw.

17 Claims, 7 Drawing Sheets

U.S. PATENT DOCUMENTS

| | | |
|---|---|---|
| 2,346,346 A | 4/1944 | Anderson |
| 2,391,537 A | 12/1945 | Anderson |
| 2,391,693 A | 12/1945 | Ettinger |
| 2,393,694 A | 1/1946 | Kirschner |
| 2,427,128 A | 9/1947 | Ettinger |
| 2,774,271 A | 12/1956 | Mano |
| 2,876,027 A | 3/1959 | Sulmonetti |
| 2,932,029 A | 5/1960 | DeNicolo |
| 3,044,512 A | 7/1962 | Jones |
| 3,154,331 A | 10/1964 | Engelhardt |
| 3,195,380 A | 7/1965 | Bicks |
| 3,509,882 A | 5/1970 | Blake |
| 3,828,791 A | 8/1974 | Santos |
| 3,961,854 A | 6/1976 | Jaquet |
| 4,135,505 A | 1/1979 | Day |
| 4,187,840 A | 2/1980 | Watanabe |
| 4,364,381 A | 12/1982 | Sher et al. |
| 4,483,334 A | 11/1984 | Murray |
| 4,548,199 A | 10/1985 | Agee |
| 4,570,625 A | 2/1986 | Harris et al. |
| 4,600,000 A * | 7/1986 | Edwards .................... 606/54 |
| 4,611,586 A | 9/1986 | Agee et al. |
| 4,620,533 A | 11/1986 | Mears |
| 4,635,634 A | 1/1987 | Santos |
| 4,700,437 A | 10/1987 | Hoshino |
| 4,785,694 A | 11/1988 | Burmester |
| 4,848,368 A | 7/1989 | Kronner |
| D303,577 S * | 9/1989 | Hammer .................... D24/190 |
| 4,922,856 A | 5/1990 | Sweeney, Jr. |
| 5,062,844 A | 11/1991 | Jamison et al. |
| 5,152,280 A | 10/1992 | Danieli |
| 5,160,335 A | 11/1992 | Wagenknecht |
| 5,207,676 A | 5/1993 | Canadell et al. |
| 5,219,349 A | 6/1993 | Krag et al. |
| 5,376,090 A | 12/1994 | Pennig |
| 5,403,313 A | 4/1995 | Lin |
| RE34,985 E | 6/1995 | Pennig |
| 5,429,637 A | 7/1995 | Hardy |
| 5,443,465 A | 8/1995 | Pennig |
| 5,451,225 A | 9/1995 | Ross, Jr. et al. |
| 5,451,226 A | 9/1995 | Pfeil et al. |
| 5,586,983 A | 12/1996 | Sanders et al. |
| 5,662,650 A | 9/1997 | Bailey et al. |
| 5,683,389 A | 11/1997 | Orsak |
| 5,702,389 A | 12/1997 | Taylor et al. |
| 5,728,095 A | 3/1998 | Taylor et al. |
| 5,741,252 A | 4/1998 | Mazzio et al. |
| 5,752,954 A | 5/1998 | Mata et al. |
| 5,891,143 A | 4/1999 | Taylor et al. |
| 5,971,984 A | 10/1999 | Taylor et al. |
| 6,030,386 A | 2/2000 | Taylor et al. |
| 6,080,153 A | 6/2000 | Mata et al. |
| 6,129,727 A | 10/2000 | Austin et al. |
| 6,203,575 B1 | 3/2001 | Farey |
| 6,217,577 B1 | 4/2001 | Hofmann |
| 6,221,072 B1 | 4/2001 | Termaten |
| 6,342,054 B1 | 1/2002 | Mata |
| 6,491,694 B1 | 12/2002 | Orsak |

\* cited by examiner

EXTERNAL FIXATOR FOR DISTAL RADIUS FRACTURES

CROSS-REFERENCE TO RELATED APPLICATIONS

This application is a continuation of U.S. Ser. No. 09/530,760, now U.S. Pat. No. 6,491,694, which is the U.S national stage entry of International Application No. PCT/US97/20258 filed on Nov. 4, 1997 and published in English as International Publication No. WO 99/22661 on May 14, 1999, the contents of which are incorporated herein by reference, which is a continuation in part of U.S. application No. 08/349,323, filed Dec. 5, 1994, now U.S. Pat. No. 5,683,389.

FILED OF THE INVENTION

The present invention relates to orthopedic surgical instrumentation, and more particularly relates to an improved fixator for use in the treatment of bone fractures such as distal radius fractures. Even more particularly, the present invention relates to an improved external fixator for the treatment of distal radius and other like bone fractures that will assist the surgeon in restoring anatomy of a fracture following an injury by allowing the surgeon to quickly manipulate the fixator to apply force to the ligaments in several directions so that the ligaments will reposition the bone fragments in their correct anatomical position and wherein the fixator includes a unique clamp arrangement that fully articulates, yet can be rigidly affixed in a selected configuration by tightening a single connector.

BACKGROUND OF THE INVENTION

One of the most common fractures that is treated in emergency rooms is a distal radius fracture sometimes classified as a Colles fracture. One of the popular methods of treating distal radius fractures is to apply an external fixator for the purpose of reducing the fracture by ligamentotaxis, which is a method of distracting the wrist to allow the ligaments to push the bone fragments back in place.

Simple distraction of the wrist is sufficient to restore the original length of the radius, but may not adequately restore other anatomical features such as the tilt angle of the radial head commonly referred to as the radial tilt and the volar tilt.

An example of a technique of multiplanar ligamentotaxis is described by Dr. John Agee in an article published in *Orthopedic Clinics of North America*, Volume 24, No. 2, April 1993 and entitled "External Fixation: Technical Advances Based Upon Multiplanar Ligamentotaxis". John Agee is the named patentee of three (3) United States patents, namely, U.S. Pat. Nos. 4,548,199; 4,611,586; and 4,922,856. The fixator developed by Dr. Agee provides a method of achieving multiplanar ligamentotaxis through gradual turning of worm screws.

Several fixation systems have been patented that relate to the holding of bone segments. An example is U.S. Pat. No. 4,483,334, issued to William Murray and entitled "External Fixation Device". The '334 patent discloses a device for holding bone segments in known relation to each other. The apparatus includes a pair of bone clamp assemblies each secured to bone pins extending from the bone segments. A bridge extends between the pin clamp assemblies and a specialized high friction universal assembly connects the bridge to each of the pin clamp assemblies.

U.S. Pat. No. 5,207,676, issued to Jose Canadell et al., relates to an external fixator with controllable damping. This external fixator disclosed in the '676 patent is for the correction and reduction of bone fragments. The apparatus comprises a bar fastened to a biocompression system on which the bar and system are disposed upon supports for fastening pins inserted into bones.

A spinal fixator reduction frame is the subject of U.S. Pat. No. 5,219,349. A reduction frame disclosed in the '349 patent is secured to shaft handles extending from the pedicle screws of a Vermont Spinal Fixator type implant. Shaft clamps secure two T-handles of the reduction frame to the shaft handles. A lower-rod assembly joins the two opposite T-frames by means of lower-rod clamps. The shaft clamps are provided with four degrees of freedom. The joint between the lower-rod assembly and T-handle is provided with five degrees of freedom. The lower-rod assembly and the T-handle are provided with power screw threads to allow for precise translational control. The shaft clamps and lower-rod clamps are provided with taper fit joints to allow for infinite rotational adjustment and fixture. An upper-rod assembly is also provided on the T-handles to produce rotation of the T-handles by providing means for changing the distance between the upper ends of the T-handles. Finger grips are provided on the upper-rod assembly to allow the surgeon to easily use one hand to either apply or monitor the force acting along the upper-rod.

The Hardy U.S. Pat. No. 5,429,637, discloses an external modular fixator for immobilization of a fracture. The apparatus includes elements functioning as clamps and receiving anchor pins to be fixed in a predetermined angular position on either side of a fracture. A mobilization relay body is configured to be attached to the fracture. The mobilization body has a device for locking which is used to lock the clamps. A fixator and the mobilization relay bodies are lockable in various chosen arrangements. The device is shown affixed to a patient's lower arm and wrist area.

The Pennig U.S. Pat. No. 5,443,465 refers to an osteosynthesis aid which is used in particular for the fixation of a pelvis and includes a central body which is formed of at least two arm or link members, each of which has an elongated slot through which a lock bolt is passed to provide a releasable clamped joint and each of which also has releasably secured ball-joint connection to an end-connecting clamp for bone-pin or bone-screw anchorage to an afflicted bone.

A Russian Patent SU 1491-492-A1 discloses a femur neck fracture osteosynthesis device that has a support in the form of plates with inclined slots for pins. The plates have apertures for pin locks. The pin locks are designed in the form of threaded rods with nuts and washers. The plates are in parallel plane with an offset greater than the sum of the thickness of the plates and the pin diameter. The plates are interconnected by connecting pieces. Pins are passed after passing through the aiming pin and are locked by the pin locks. This device has an advantage of simplifying the design by allowing crossing-over angle in the planes parallel with the femur axis.

A patent that relates generally to orienting and securing a rod in a spatially adjusted position is the subject of the Jaquet U.S. Pat. No. 3,961,854, entitled "Apparatus For Orienting And Maintaining A Rod In Any Direction". The Jaquet patent discusses maintaining an object which one desires to place in diverse orientations as for example, a table lamp, a reflector, and also to employ the same in surgical uses.

SUMMARY OF THE INVENTION

The present invention provides an improved bone fixator that enables the orthopedic surgeon to restore the patient's anatomy at a fracture following an injury. The present invention enables a surgeon to quickly manipulate the fixator and an articulating clamp (or clamps) to apply force to the ligaments in several directions so that the ligaments will reposition the bone fragments in their correct anatomical position and wherein a single fastener is tightened to rigidify the clamp and bone parts connected thereto.

Multiple pin clamps are placed along a rod to secure the rod to the bone. The pin clamps allow rotation around the bar as well as rotation around the clamp to allow the pins to be placed at a wide variety of angles and in multiple planes. A double pin clamp can be used to secure pins into selected bone parts such as the metacarpals of the hand. The multiple pin clamp also allows rotation about two axes. It can be rigidified in a selected position with a single fastener.

In the preferred embodiment, the pins are secured to the clamp by set screws. However, other clamping methods may be used (for example, clam shell clamps). The restoration of anatomical length is achieved by sliding the pin clamps along the rod to distract the ligaments.

For a wrist fracture, restoration of the volar tilt is achieved by loosening the set screws on the metacarpal pin clamp and rotating the rod to allow a vertical translation of the metacarpal pin clamp. Radial tilt can be restored by translating the metacarpal pins through the clamp to shift the wrist sideways. In extreme cases, the rotation can be adjusted by tightening the metacarpal pin clamp to the rod and rotating the rod.

The present invention provides an improved fixator apparatus for distal radius fractures that includes an elongated support rod having proximal and distal rod sections joined by a transverse rod section that offsets the proximal and distal rod sections. A pair of bends integrally joins the proximal and distal rod sections to the transverse rod section. Radius fixation pins are provided for engaging a patient's radius bone tissue.

Radius support clamps are rotatably supported upon the proximal rod section for externally supporting the patient's distal radius, the support clamps including openings that support the radius fixation pins. The support clamps allow rotation relative to the rod and relative to the radius fixation pins. Metacarpal fixation pins are provided for engaging the patient's metacarpal bone tissue.

Hand support clamps are rotatably supported upon the distal rod section for externally supporting the patient's hand. The hand support clamps include openings for holding the metacarpal fixation pins, the hand support clamps allowing rotation relative to the rod and relative to the metacarpal fixation pins. The proximal and distal rod sections are preferably generally parallel.

The proximal rod section has a central longitudinal axis and the radius support clamp and rod are so configured that the distal rod section is rotatable during use about the central longitudinal axis of the proximal rod section.

The metacarpal support clamp is slidable along the distal rod section during use for distracting the ligaments of the patient's wrist.

The rod and support clamps are so configured that volar tilt is achieved by rotating the distal rod section relative to the proximal rod section when the support clamps are rotated with respect to the rod.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE PREFERRED EMBODIMENT

Figure 1:
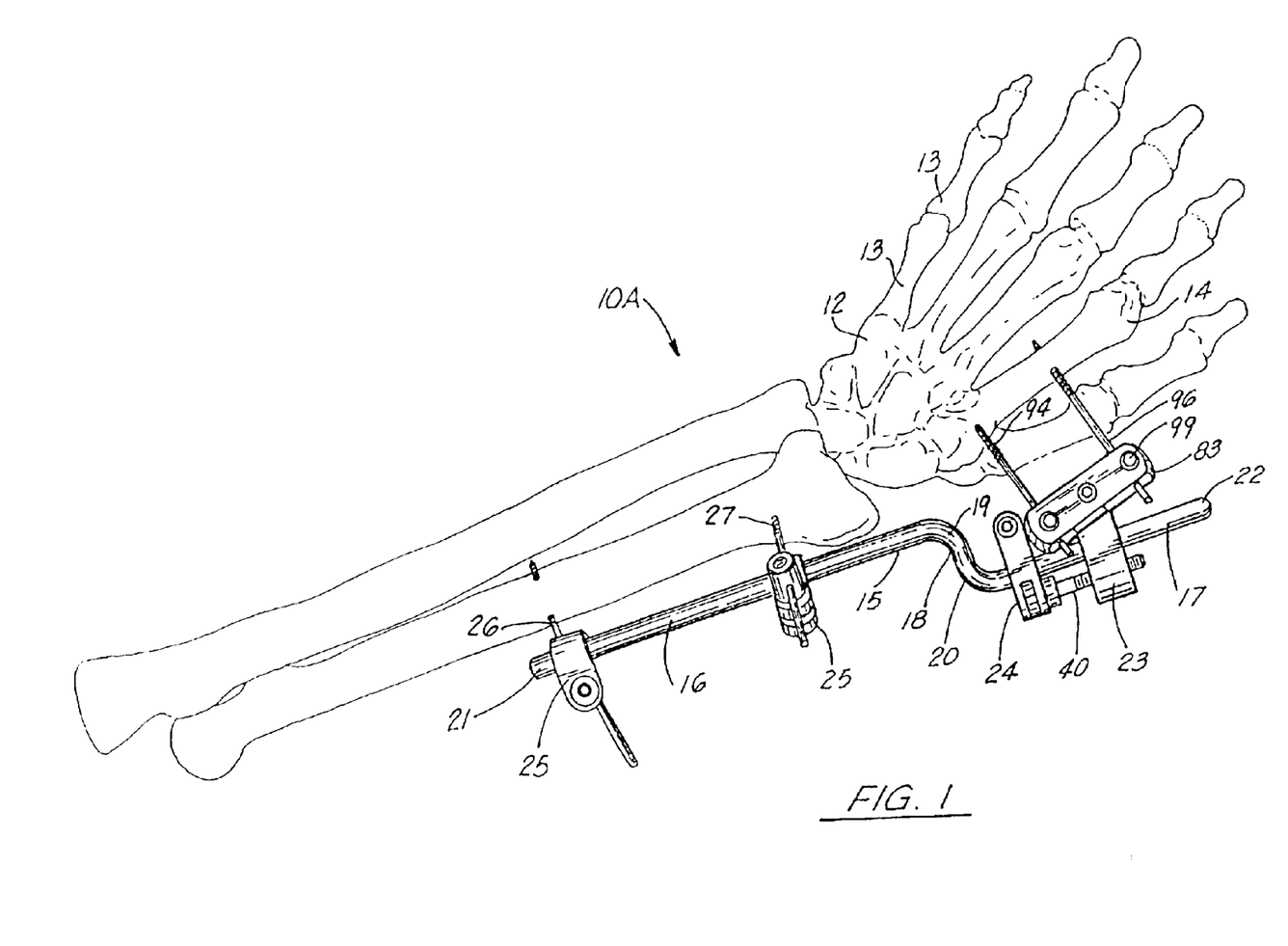
FIG. 1 is a perspective view of a first embodiment of the apparatus of the present invention.
Figure 2:
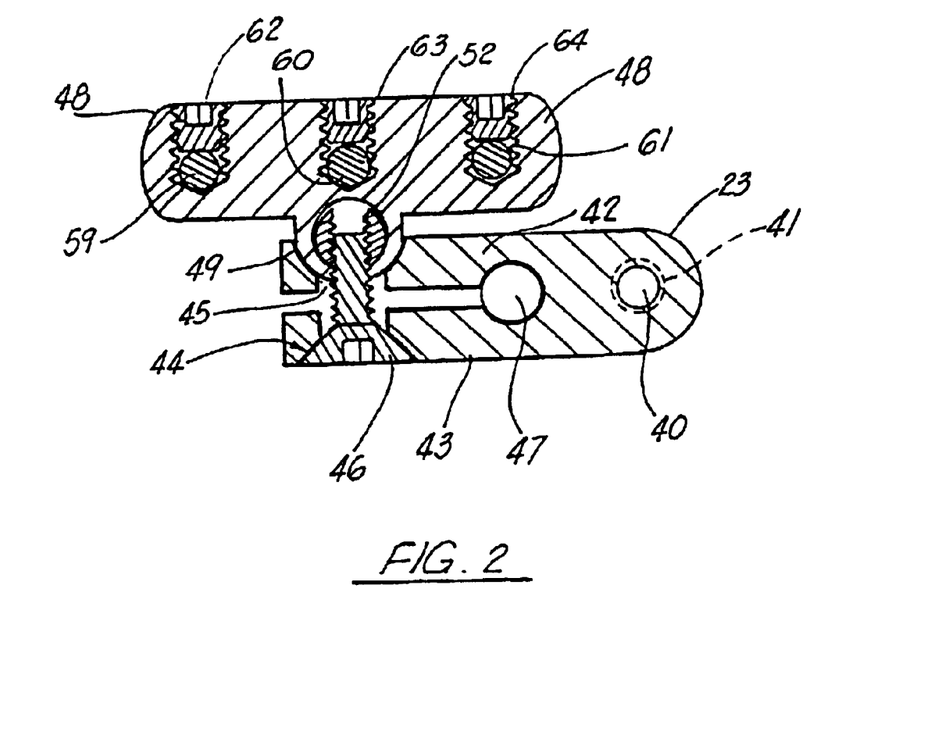
FIG. 2 is a partial sectional view of the first embodiment of the apparatus of the present invention.

FIGS. 1–4 show generally the first embodiment of the apparatus of the present invention designated generally by the numeral 10 in FIG. 1. Fixator 10A is shown in FIG. 1 can be attached to a patient's fractured bone such as the distal radius 11, wrist 12 and hand 13 at metacarpals 14.

An elongated rod 15 includes a proximal rod section 16 and a distal rod section 17. Rod sections 16 and 17 are preferably joined by a transverse rod section 18 and a pair of bends 19, 20. The rod 15 is preferably integrally formed as shown, including proximal and distal rod sections 16, 17, transverse rod section 18, and bends 19, 20. The rod ends 21, 22 can be provided with protective plastic end caps (not shown) to contain the pin clamps on the rod when the clamps are loosened.

One or more clamps 25 can be attached to proximal rod section 16. In FIG. 1, a single radius pin clamp 25 is shown in the illustration. Each of the radius pin clamps 25 affixes to the radius bone pins 26, 27 as shown. The construction of pin clamps 25 is shown more particular in the parent patent application U.S. Ser. No. 08/349,323, filed Dec. 5, 1994, now U.S. Pat. No. 5,683,389 which is incorporated herein by reference. Each radius pin 26, 27 is surgically connected to the fractured radius 11 as shown.

Figures 3, 4:
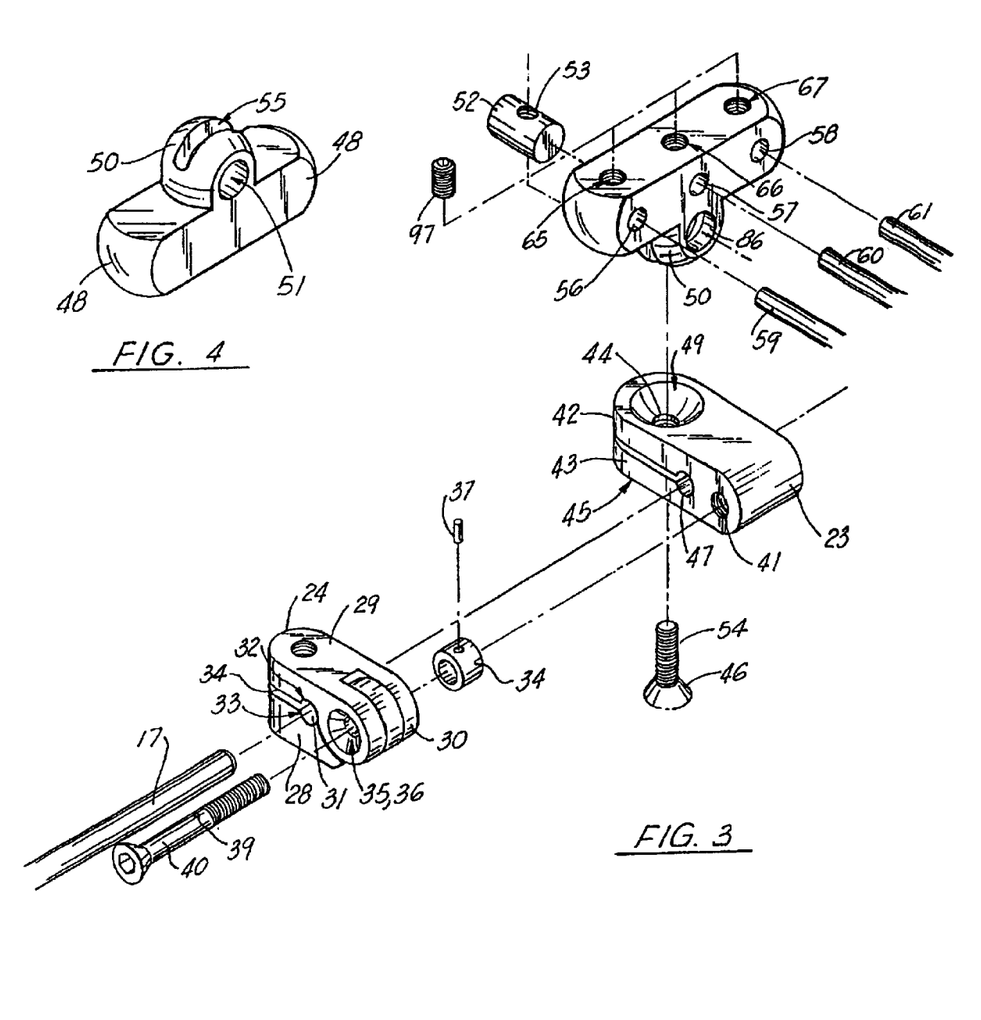
FIG. 3 is a partial perspective exploded view of the first embodiment of the apparatus of the present invention.
FIG. 4 is a partial perspective view of the first embodiment of the apparatus of the present invention.
Figure 5:
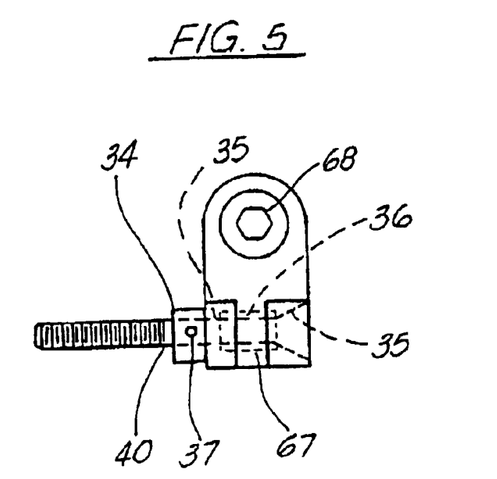
FIG. 5 is a partial side view of the first embodiment of the apparatus of the present invention.
Figure 6:
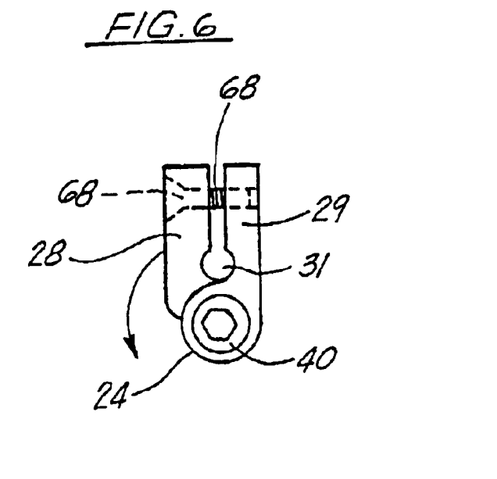
FIG. 6 is a partial end view of the first embodiment of the apparatus of the present invention.

Fixator 10A also provides a distraction mechanism that can be used in combination with an improved, easily adjustable articulating clamp 23 as shown at the distal rod section 17 in FIG. 1. Distraction clamp mechanism 24 clamps to proximal rod section 17 nearer to transverse rod section 18 Articulating clamp 23 is positioned in between distraction clamp 24 and rod end 22. In FIGS. 1 and 3–6, distraction clamp 24 includes a pair of clamp members 28, 29 that are hingedly connected together at hinge 30. A cylindrically shaped recess 31 is defined upon a closure of distraction clamp 24 as shown in FIG. 3. Each clamp member 28, 29 provides a respective half cylinder shaped slot 32, 33 that together define the cylindrical recess 34 upon closure.

Hinge 30 includes aligned openings in each clamp member 28, 29 that align and mount to bushing 34. Each of the clamp members 28, 29 has an opening 35, 36 respectively that fits over bushing 34. Each clamp member 28, 29 opening 35, 36 is cylindrically shaped and sized to closely fit the external surface and diameter of bushing 34. Pin 37 fits through opening 38 in bushing 34 and then through bolt 40 at opening 39. Countersunk distraction clamp bolt 40 extends through bushing 34 and engages articulating clamp 23 at internally threaded cylindrical opening 41. Clamp 23 includes a pair of spaced apart flanges 42, 43. Each flange 42, 43 provides an opening 44, 45, respectively for accommodating bolt 46. The clamp 23 includes a generally cylindrically shaped slot 47 that is generally parallel to threaded opening 41 and bolt 40 as shown in FIG. 3. Slot 47 engages distal section 17 of rod 15 during use.

Pin block 48 attaches to clamp 23 at hemispherical recess 49. Pin block 48 provides a correspondingly shaped hemispherical projection 50 that engages recess 49 as shown in FIG. 3. A cylindrically shaped opening 51 receives pin 52. Pin 52 has internally threaded opening 53 for receiving the threaded shaft 54 of machine screw 46.

Hemispherical projection 50 has an arcuate slot 55 that allows threaded shaft 54 of screw 46 to pass therethrough. This allows the projection 50 to articulate with respect to recess 49 and clamp flanges 42, 43. Pin block 48 includes a plurality of openings 56–58 that accommodate a plurality of bone pins such as the pins 59–61. Pins 59–61 are surgically affixed to the patient's bone tissue as seen in FIG. 1. Set screws 62–64 are used to affix each pin 59–61 to pin block 48. Each set screw 62–64 travels in a threaded opening 65–67 respectively of pin block 48.

In order to articulate pin block 48 relative to flanges 42, 43 the user simply loosens machine screw 46. This allows articulation of block 48 in multiple directions and into multiple angular positions with reference to flanges 42, 43 and distal rod 17. Pin block 48 is free to rotate and pivot with reference to rod 17 when machine screw 46 is loosened. Clamp 23 can be attached to rod 17 as shown in FIG. 1. Clamp 23 can also travel longitudinally along rod or rotate about rod section 17 for adjustment.

Distraction can be achieved by fixedly clamping distraction clamp 28 to rod section 17 by tightening set screw 68. A loosening of screw 68 allows clamp 28 to be adjusted into desired positions on rod distal end section 17. Once set screw 68 is tightened, the user can then move clamp 23, the attached pins 59–61 and the surgically pinned metacarpals 14 relative to clamp 24 by rotating screw 40 thereby accomplishing the desired distraction.

Figure 7:
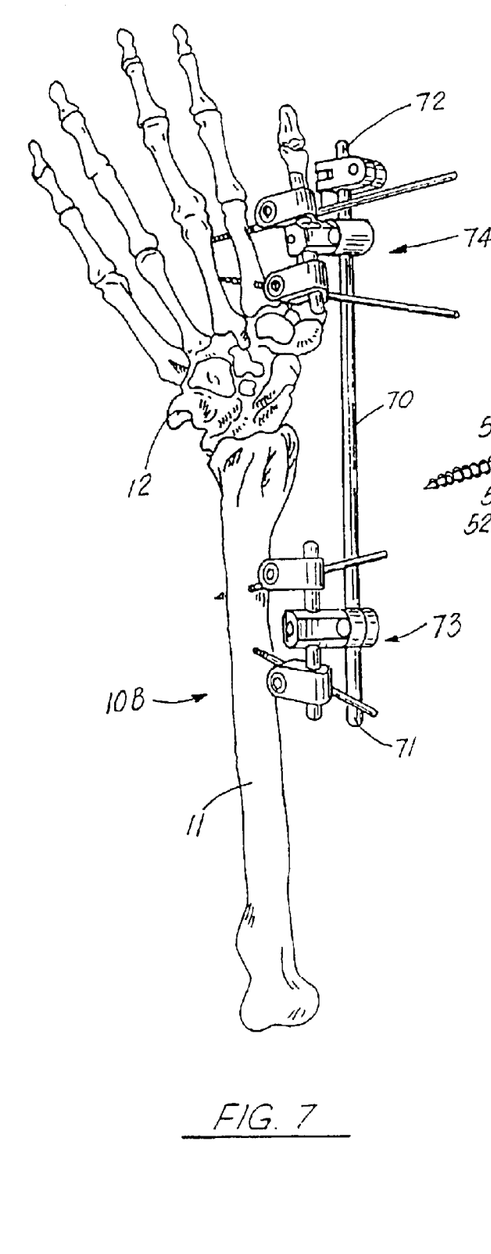
FIG. 7 is a perspective view of the second embodiment of the apparatus of the present invention affixed to a patient's wrist area.

FIGS. 7–12 show a second embodiment of the apparatus of the present invention, designated generally by the numeral 10B in FIG. 7. Fixator apparatus 10B utilizes rod 70 having proximal 71 and distal 72 end portions and a generally straight, linear central longitudinal axis. The embodiment of FIG. 7 can use multiple clamps such as the clamp 23 of FIGS. 1–3 and 8 or the clamp assemblies 73–74 of FIGS. 9–12. In FIG. 7, the fixator apparatus is shown with two articulating clamp assemblies 73 (see also FIG. 10), 74 (see also FIG. 11) on a patient's distal radius 11 and wrist 12.

Figure 8:
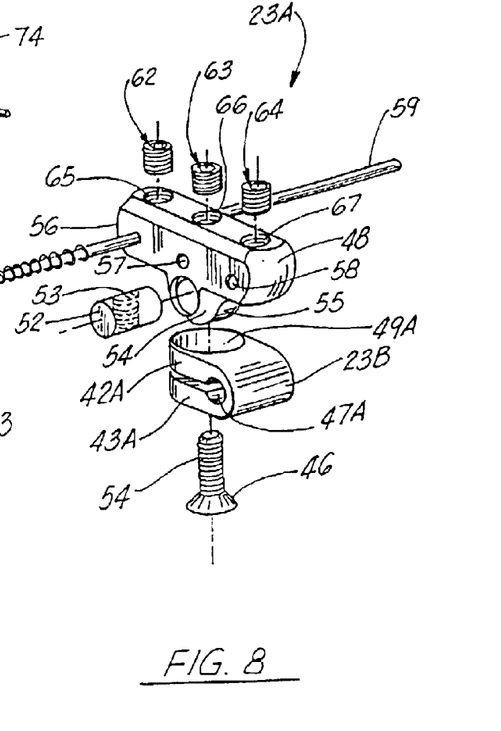
FIG. 8 is a partial perspective exploded view of a clamp that can be used with the first and second embodiments of the apparatus of the present invention.

In FIG. 8, the clamp 23A shown is similar to the clamp 23 of FIG. 3, but without the distraction mechanism that is a part of the clamp 23 in FIG. 3. In FIG. 8, the clamp 23A has a clamp body 23B that is comprised of a pair of flanges 42A, 43A having a gap therebetween. Cylindrically-shaped opening 47A conforms to the outer surface of rod 70. The pin block 48 is the same construction as that shown in FIG. 3, including openings 56A-58 for accepting pins 59–61 and set screws 63–64. Opening 65–67 receive the set screws 62–64. Nut 52 connects with bolt 46. The threads 54 of bolt 46 engage the internal threads 53 of nut 52 as with the embodiment of FIG. 3.

Figure 9:
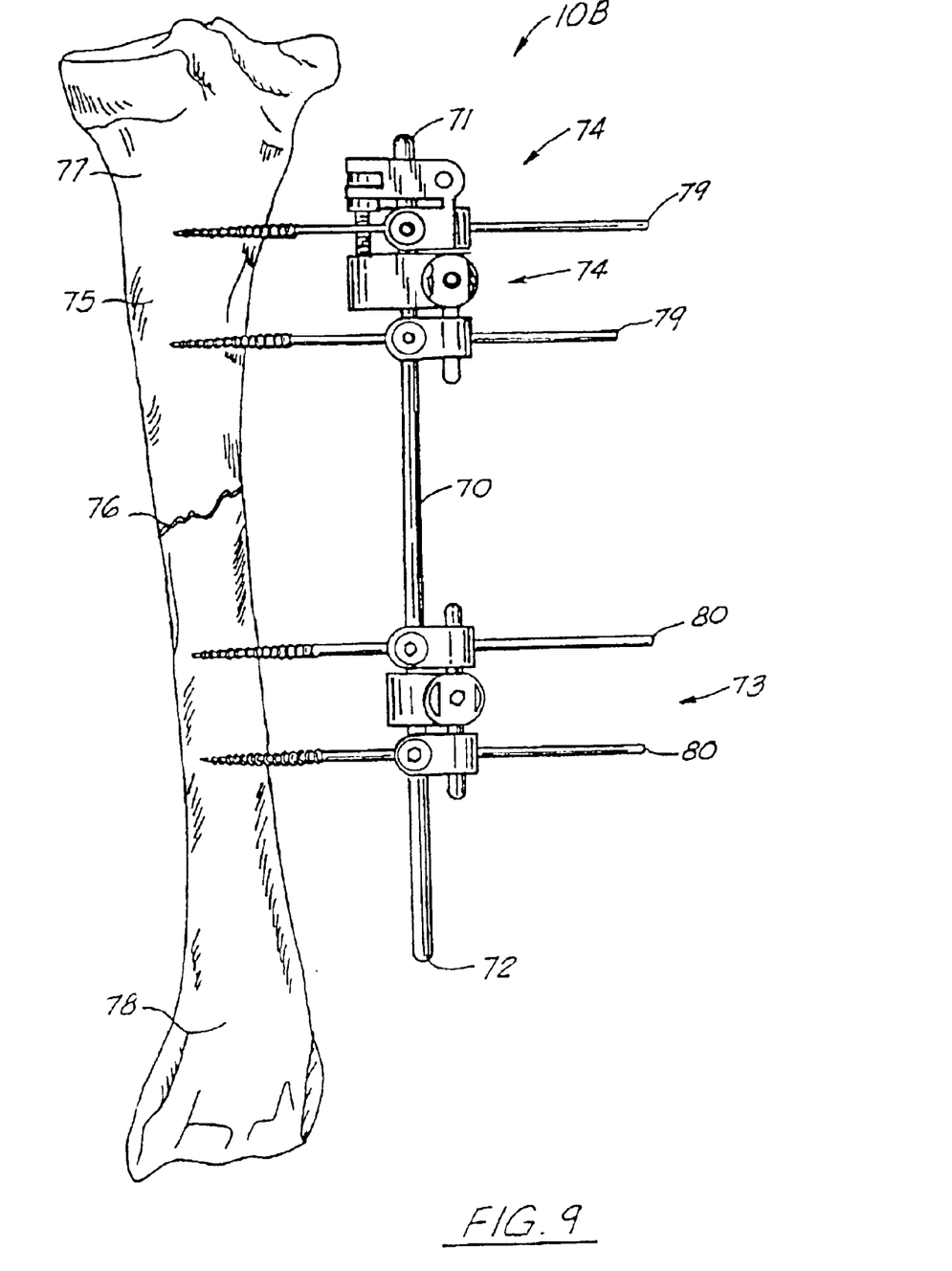
FIG. 9 is a perspective view of the second embodiment of the apparatus of the present invention shown attached to a patient's leg bone.
Figure 10:
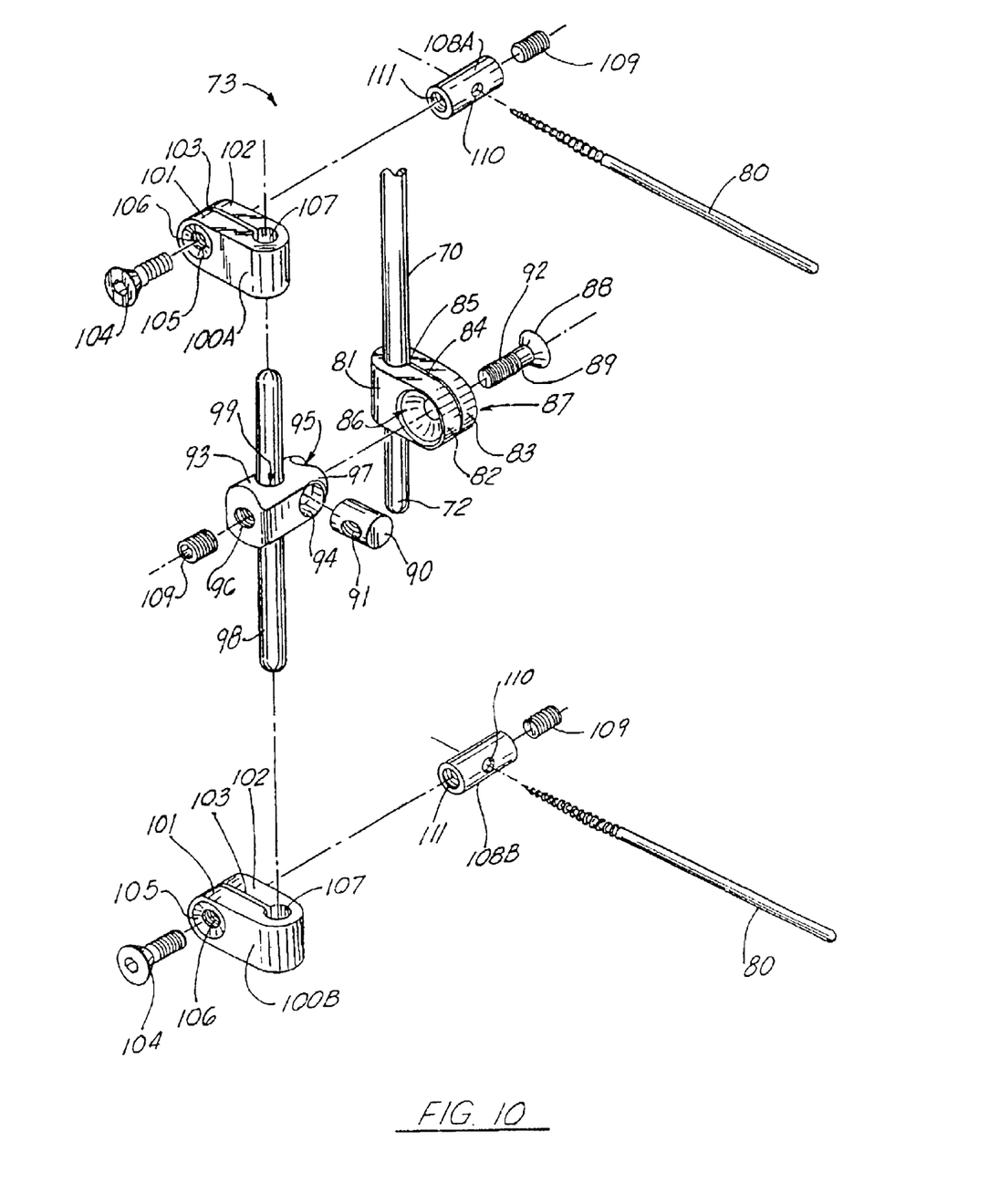
FIG. 10 is a partial perspective view of the second embodiment of the apparatus of the present invention.
Figure 11:
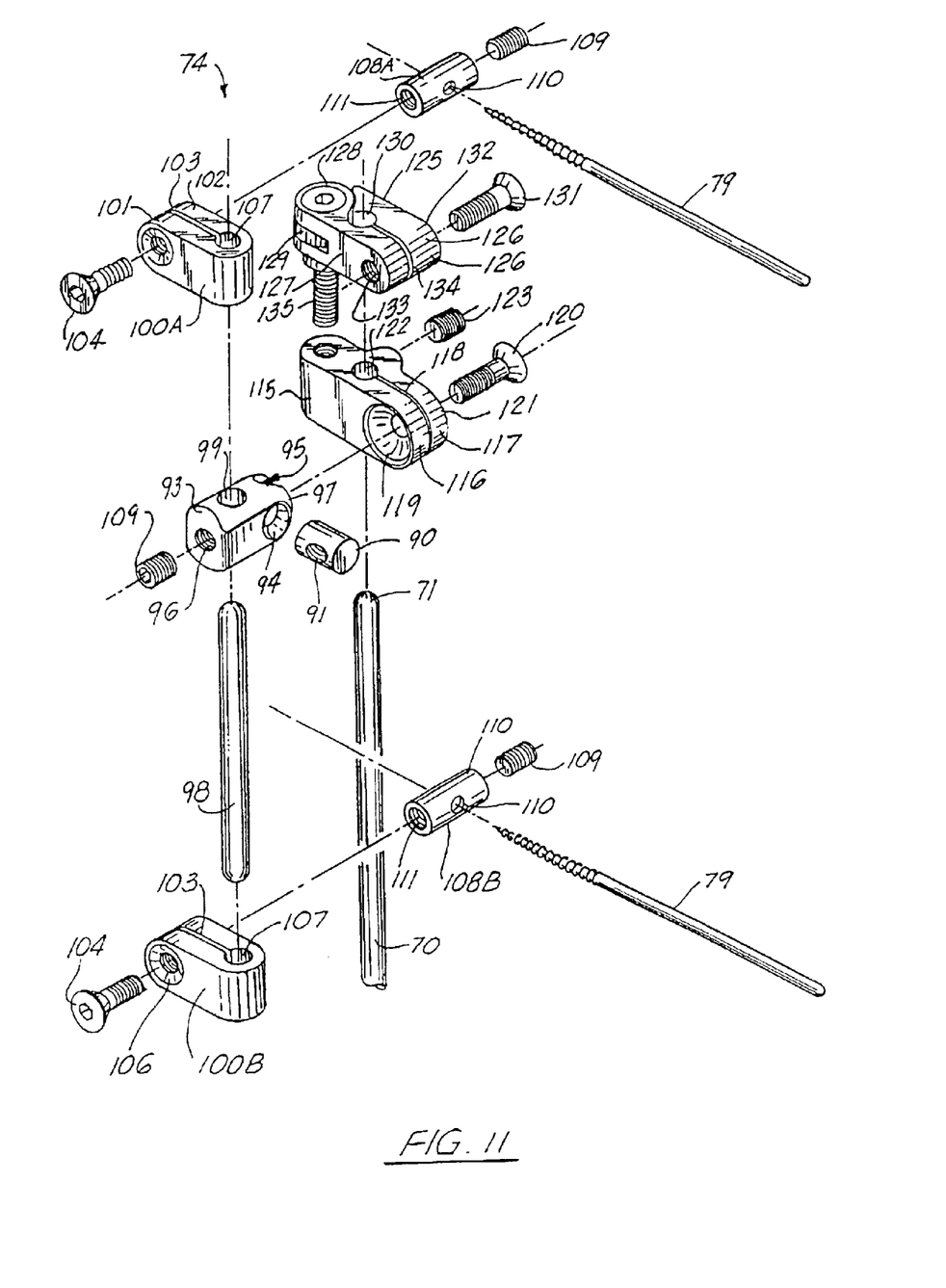
FIG. 11 is a partial exploded perspective view of the second embodiment of the apparatus of the present invention.

The construction of clamps 73 and 74 is shown more particularly in FIGS. 10 and 11 respectively. FIG. 9 shows the second embodiment of the apparatus of the present invention connected to a patient's leg bone 75. In FIG. 9, the leg bone 75 is shown as a fractured leg bone. The fracture site 76 has broken the bone 75 into a proximal bone segment 77 and a distal bone segment 78. Proximal bone pins 79 are affixed to the proximal bone segment 75. Similarly, distal bone pins 80 are affixed to the distal bone segment 78 as shown in FIG. 9. In FIG. 10, the clamp assembly 73 includes a clamp body 81 having a pair of flanges 82, 83 with gap 84 therebetween. A cylindrical recess 85 enables the clamp body 81 to be attached to rod 70 as shown in FIG. 10. Hemispherical recess 86 on clamp body 81 accepts projecting portion 97 of block 93. Flange 83 has a countersunk recess 87 that receives the conical head 88 of set screw 89. Each of the flanges 82, 83 has an opening so that the set screw 89 can pass through the flanges 82, 83 and form a connection with nut 90 when the external threads 92 of set screw 89 engage the internally threaded opening 91 of nut 90. This occurs when the nut 90 occupies cylindrical bore 94 of block 93. An arcuate slot 95 enables the block 93 to angulate relative to set screw 89 and clamp body 81 when the set screw 89 is loosened slightly. The set screw 89 can also be loosened so that the block 93 rotates with respect to clamp body 81. This combination of angulation and rotation of block 93 relative to clamp body 81 provides an almost universal articulating connection between the primary rod section 70 and secondary rod section 98. The rod section 98 occupies cylindrical bore 99 of block 93. The block 93 can slide along rod 98 and be affixed thereto at a selected position using set screw 109 that threadably engages the internally threaded opening 96 in block 93. The internally threaded opening 96 communicates with bore 99 so that when the user tightens the set screw 109 it engages the outer surface of rod 98.

Secondary rod 98 carries a pair of clamps 100A, 100B. The clamp 100A has a pair of flanges 101, 102 with a gap 103 therebetween. Set screw 104 extends through openings in flanges 101, 102 and engages internally threaded sleeve 108A at the cylindrically shaped internally threaded bore 111 thereof. Cylindrical opening 110 through sleeve 108A receives a distal bone pin 80. Set screw 109 also engages internally threaded bore 111 to form a clamped connection with pin 80 holding it in a selected position.

Clamp 100B includes a pair of flanges 101, 102 with a gap 103 therebetween. Opening 106 receives set screw 104. The set screw 104 is externally threaded to engage the internally threaded bore 111 of sleeve 108B. Opening 110 in sleeve 108B receives bone pin 80. Set screw 109 engages internally threaded bore 111 of sleeve 108B to clamp bone pin 80 in a selected position. Openings 107 in the clamps 100A, 100B enable the clamps 100A, 100B to be mounted on rod secondary rod section 98. Each of the clamps 100A, 100B can have a countersunk recess 105 at flange 100 for cooperating with a correspondingly shaped head portion of set screw 104.

In FIG. 11, clamp 74 is shown. Clamp 74 is similar in construction to the clamp 73 of FIG. 10 but with an added distraction feature. The clamp 74 includes secondary rod 98, block 93, and clamps 100A, 100B. However, a distraction clamp body 115 mounts to primary rod 70 at cylindrical bore 122. Clamp body 115 includes a pair of flanges 116, 117 with a gap 118 therebetween. Hemispherically-shaped recess 119 receives the projecting portion 97 of block 93. Set screw 120 cooperates with a countersunk opening 121 portion of flange 117. An opening in each of the flanges 116, 117 allows set screw 120 to pass through flanges 116, 117 in order to engage nut 90 at its internally threaded opening 91. As with the clamp 73 of FIG. 10, slot 95 allows angulation between block 93 and clamp body 115. Clamp body 115 provides a cylindrically-shaped opening 122 that is sized and shaped to fit the outside surface of rod 70. Set screw 123 engages a correspondingly shaped internally threaded opening that extends through clamp body 115 to communicate with bore 122. In this fashion, a user simply tightens the set screw 123 to affix the rod 70 with respect to the clamp body 115 in a desired position.

Internally threaded opening 124 receives threaded shaft 135 of bolt 128. Clamp body 125 carries bolt 128. The clamp body 125 is comprised of a pair of clamped members 126, 127 that are hingedly connected together at hinge 129. A cylindrically-shaped recess 130 enables rod 70 to extend through clamp body 125. Set screw 131 engages internally threaded openings 132, 133 and the clamp members 126, 127. This enables the set screw 131 to be tightened, closing the gap 134 and clamping the clamp body 125 to rod 70.

During use, a very universal articulating connection can thus be formed between either of the clamps 73 or 74 and rod 70 relative to bone parts 77, 78 or a patient's radius 11 and wrist 12. This is accomplished by the ability to rotate the clamp body 81 relative to rod 70, or the clamp body 115 relative to the rod 70. Further, the block 93 of either clamp 73 or 74 can articulate and rotate relative to the clamp body 81 or 115. Additionally, the connection between rod 98 and block 93 is a sliding and rotating connection. Further, each block 93 can angulate relative to its associate clamp body 81 or 115. The clamps 100A, 100B can slide along secondary rod 98 or rotate with respect thereof. Further, the bone pins 79 and 80 can rotate with respect to the clamps 100A, 100B. Additionally, the bone pins 79 and 80 can slide in their respective sleeves 100A, 100B.

The following table lists the parts numbers and parts descriptions as used herein and in the drawings attached hereto.

PARTS LIST

| Part Number | Description |
|---|---|
| 10A | fixator apparatus |
| 10B | fixator apparatus |
| 11 | distal radius |
| 12 | wrist |
| 13 | hand |
| 14 | metacarpals |
| 15 | rod |
| 16 | proximal rod section |
| 17 | distal rod section |
| 18 | transverse rod section |
| 19 | bend |
| 20 | bend |
| 21 | rod end |
| 22 | rod end |
| 23 | clamp |
| 23A | clamp |
| 23B | clamp body |
| 24 | distraction clamp mechanism |
| 25 | radius pin clamp |
| 26 | radius pin |
| 27 | radius pin |
| 28 | clamp member |
| 29 | clamp member |
| 30 | hinge |
| 31 | recess |
| 32 | slot |
| 33 | slot |
| 34 | bushing |
| 35 | opening |
| 36 | opening |
| 37 | pin |
| 38 | opening |
| 39 | opening |
| 40 | bolt |
| 41 | opening |
| 42 | flange |
| 42A | flange |
| 43 | flange |
| 43A | flange |
| 44 | opening |
| 45 | opening |
| 46 | bolt |
| 47 | opening |
| 47A | opening |
| 48 | pin block |
| 49 | recess |
| 49A | recess |
| 50 | hemispherical projection |
| 51 | opening |
| 52 | nut |
| 53 | internally threaded opening |
| 54 | threaded shaft |
| 55 | slot |
| 56 | opening |
| 57 | opening |
| 58 | opening |
| 59 | pin |
| 60 | pin |
| 61 | pin |
| 62 | set screw |
| 63 | set screw |
| 64 | set screw |
| 65 | threaded opening |
| 66 | threaded opening |
| 67 | threaded opening |
| 68 | set screw |
| 69 | |
| 70 | rod |
| 71 | proximal end |
| 72 | distal end |
| 73 | clamp assembly |
| 74 | clamp assembly |
| 75 | leg bone |
| 76 | fracture site |
| 77 | proximal bone segment |
| 78 | distal bone segment |
| 79 | bone pin, proximal |
| 80 | bone pin, distal |
| 81 | clamp body |
| 82 | flange |
| 83 | flange |
| 84 | gap |
| 85 | cylindrical recess |
| 86 | hemispherical recess |
| 87 | countersunk recess |
| 88 | conical head |
| 89 | set screw |
| 90 | nut |
| 91 | internally threaded opening |
| 92 | external threads |
| 93 | block |

-continued

PARTS LIST

| Part Number | Description |
| --- | --- |
| 94 | cylindrical bore |
| 95 | arcuate slot |
| 96 | internal threaded opening |
| 97 | projecting portion |
| 98 | rod |
| 99 | cylindrical bore |
| 100A | clamp |
| 100B | clamp |
| 101 | flange |
| 102 | flange |
| 103 | gap |
| 104 | set screw |
| 105 | countersunk recess |
| 106 | internally threaded opening |
| 107 | cylindrical bore |
| 108A | internally threaded sleeve |
| 108B | internally threaded sleeve |
| 109 | set screw |
| 110 | cylindrical opening |
| 111 | internally threaded bore |
| 115 | distraction clamp body |
| 116 | flange |
| 117 | flange |
| 118 | gap |
| 119 | hemispherically-shaped recess |
| 120 | set screw |
| 121 | countersunk opening |
| 122 | cylindrical bore |
| 123 | set screw |
| 124 | internally threaded opening |
| 125 | clamp body |
| 126 | clamp member |
| 127 | clamp member |
| 128 | bolt |
| 129 | hinge |
| 130 | cylindrically-shaped recess |
| 131 | set screw |
| 132 | countersunk opening |
| 133 | internally threaded bore |
| 134 | gap |
| 135 | threaded shaft |

The foregoing embodiments are presented by way of example only; the scope of the present invention is to be limited only by the following claims.

What is claimed is:

1. An external fixator apparatus for fixating bone parts at a fracture site comprising:
    an elongated support rod;
    fixation pins for engaging a patient's bone parts on opposing sides of the fracture site; and
    a pair of support clamps supported upon the support rod for externally supporting the bone pins and the patient's bone parts, at least one of the clamps comprising:
        a rod attachment structure with an opening configurable to engage the support rod and with a substantially hemispherical recess; and
        a pin block with a substantially spherical projection, the pin block being configurable to accommodate a fixation pin and to engage in the substantially hemispherical recess with the substantially spherical projection;
        wherein a fastener passes through at least part of the substantially hemispherical recess and the substantially spherical projection such that by operating the fastener, motion between the rod attachment structure and the pin block is restricted.

2. The fixator apparatus of claim 1 wherein the pin block holds multiple pins.

3. The fixator apparatus of claim 1 wherein the pin block is adjustably positionable relative to the rod attachment structure.

4. The fixator apparatus of claim 1 wherein the pin block and the rod attachment structure can rotate relative to one another when the fastener is loosened.

5. The fixator apparatus of claim 3 wherein the pin block and the rod attachment structure can angulate relative to one another when the fastener is loosened.

6. The fixator apparatus of claim 1 wherein the pin block and the rod attachment structure can simultaneously rotate and angulate relative to one another when the fastener is loosened.

7. The fixator apparatus of claim 1 wherein the rod has a central linear longitudinal is.

8. The fixator apparatus of claim 1 wherein the clamps are slidable on the support rod during use.

9. The fixator apparatus of claim 1 wherein by operating the fastener, motion between the rod attachment structure and the pin block, and between the rod attachment structure and the support rod is restricted.

10. An external fixator apparatus for fixating bone parts at a fracture site comprising:
    an elongated support rod;
    fixation pins for engaging a patient's bone parts on opposing sides of the fracture site; and
    a pair of support clamps supported upon the support rod for externally supporting the bone pins and the patient's bone parts, at least one of the clamps comprising:
        a rod attachment structure with an opening configurable to engage the support rod and with a substantially hemispherical recess; and
        a block with a substantially spherical projection, the block being configurable to accommodate a second rod and to engage in the substantially hemispherical recess with the substantially spherical projection;
        wherein a fastener passes through at least part of the substantially hemispherical recess and the substantially spherical projection such that by operating the fastener, motion between the rod attachment structure and the block is restricted;
        a connector captured by the block; and
        at least two members mounted on the connector, each member adapted to capture a fixator pin.

11. The fixator apparatus of claim 10 wherein at least one of the members is adjustably mounted to the connector.

12. The fixator apparatus of claim 10 wherein the block and the rod attachment structure can rotate relative to one another when the fastener is loosened.

13. The fixator apparatus of claim 10 wherein the block and the rod attachment structure can angulate relative to one another when the fastener is loosened.

14. The fixator apparatus of claim 10 wherein the block and the rod attachment structure can simultaneously rotate and angulate relative to one another when the fastener is loosened.

15. The fixator apparatus of claim 10 wherein the support rod has a central linear longitudinal axis.

16. The fixator apparatus of claim 10 wherein the clamps are slidable on the support rod during use.

17. The fixator apparatus of claim 10 wherein by operating the fastener, motion between the rod attachment structure and the block, and between the rod attachment structure and the support rod is restricted.

* * * * *